United States Patent [19]

Leet

[11] Patent Number: 5,143,906

[45] Date of Patent: Sep. 1, 1992

[54] KEDARCIDIN ANTITUMOR CHROMOPHORE AND PHARMACEUTICAL COMPOSITION CONTAINING SAME

[75] Inventor: John E. Leet, Wallingford, Conn.

[73] Assignee: Bristol-Myers Squibb Company, New York, N.Y.

[21] Appl. No.: 763,465

[22] Filed: Sep. 26, 1991

[51] Int. Cl.⁵ .................. A61K 31/70; C07H 17/00
[52] U.S. Cl. ......................... 514/30; 514/28; 514/53; 536/16.8; 536/17.4; 536/18.1
[58] Field of Search ............ 536/17.4, 18.1, 127; 514/12, 28, 30, 53; 435/16.8

[56] References Cited

U.S. PATENT DOCUMENTS 3,706,729 12/1972 Batcho et al. .................. 536/17.4
5,001,112 3/1991 Hofstead et al. .................. 514/12

OTHER PUBLICATIONS

Otto D. Hensens et al., *The Journal of Antibiotics*, 1989, 42, 761–768.
H. Suzuki et al., *Biochemical and Biophysical Research Communications*, 1980, 94, 255–261.

Primary Examiner—Johnnie R. Brown
Assistant Examiner—A. Rahman
Attorney, Agent, or Firm—David M. Morse

[57] ABSTRACT

Kedarcidin chromophore, a non-protein chromophore isolated from kedarcidin antitumor antibiotic, is obtained from purified or partially purified kedarcidin by solvent extraction and chromatographic procedures. The chromophore is characterized and found to contain substantially all of the antitumor activity of kedarcidin.

2 Claims, 4 Drawing Sheets

KEDARCIDIN ANTITUMOR CHROMOPHORE AND PHARMACEUTICAL COMPOSITION CONTAINING SAME

DESCRIPTION OF THE PRIOR ART

The protein antitumor antibiotic designated kedarcidin is disclosed in U.S. Pat. No. 5,001,112. This antibiotic is reported to be a complex of a single chain polypeptide and a non-protein chromophore. The kedarcidin antibiotic is produced by fermentation of Streptoalloteichus sp. nov. strain L585-6 (ATCC-53650) and the isolation and purification of kedarcidin are described in Example 4 of the aforementioned U. S. patent. The patent reference does not disclose or suggest any procedure for separating the chromophore from the isolated kedarcidin antibiotic nor does it suggest that the antitumor activity of kedarcidin resides in the non-protein chromophore.

The antitumor antibiotic designated neocarzinostatin consists of a 1:1 complex of a protein and a non-protein chromophore. The literature discloses that the chromophore moiety of neocarzinostatin can be separated from the neocarzinostatin complex by extraction with acidic methanol and that the antitumor properties of neocarzinostatin reside mainly in the chromophore. In the case of neocarzinostatin, the structure of the chromophore has been determined (see, for example, *J. Antibiotics*, 1989, 42, 761-768. In the case of kedarcidin, however, the methanol extraction procedure was not satisfactory to obtain the purified chromophore.

Another protein antitumor antibiotic designated aureomycin also contains a protein component and a non-protein chromophore. The chromophore of this antibiotic was also separated from the antibiotic by methanol extraction (see *Biochem. Biophys. Res. Commun.*, 1980, 94, 255-261, and the antitumor activity was again found primarily in the chromophore.

Applicant is aware of other protein antitumor antibiotics containing a non-protein chromophore where the chromophore was not able to be successfully separated from the antibiotic either with the methanol extraction procedure described above or with other conventional purification procedures. In general, the chromophores of such protein antibiotics, even if they can be separated and isolated, are much more unstable than the antibiotic complex per se.

SUMMARY OF THE INVENTION

The present invention relates to a novel antitumor chromophore obtained from kedarcidin antibiotic.

The present invention also provides a process for the production of kedarcidin chromophore which comprises the steps of (a) providing an aqueous solution of kedarcidin; (b) subjecting said aqueous solution to organic extraction with ethyl acetate; (c) collecting the ethyl acetate extract; (d) subjecting said ethyl acetate extract to silica gel column chromatography using a benzene-methanol step gradient eluant; and (e) collecting the fraction containing the kedarcidin chromophore.

Another aspect of the present invention is a method for inhibiting tumor growth in a mammalian host which comprises administering to said host a tumor-inhibiting amount of kedarcidin chromophore or a pharmaceutical composition thereof.

The present invention also provides a pharmaceutical composition comprising a tumor-inhibiting amount of kedarcidin and a pharmaceutically acceptable carrier of diluent.

DETAILED DESCRIPTION OF THE INVENTION

Figure 1:
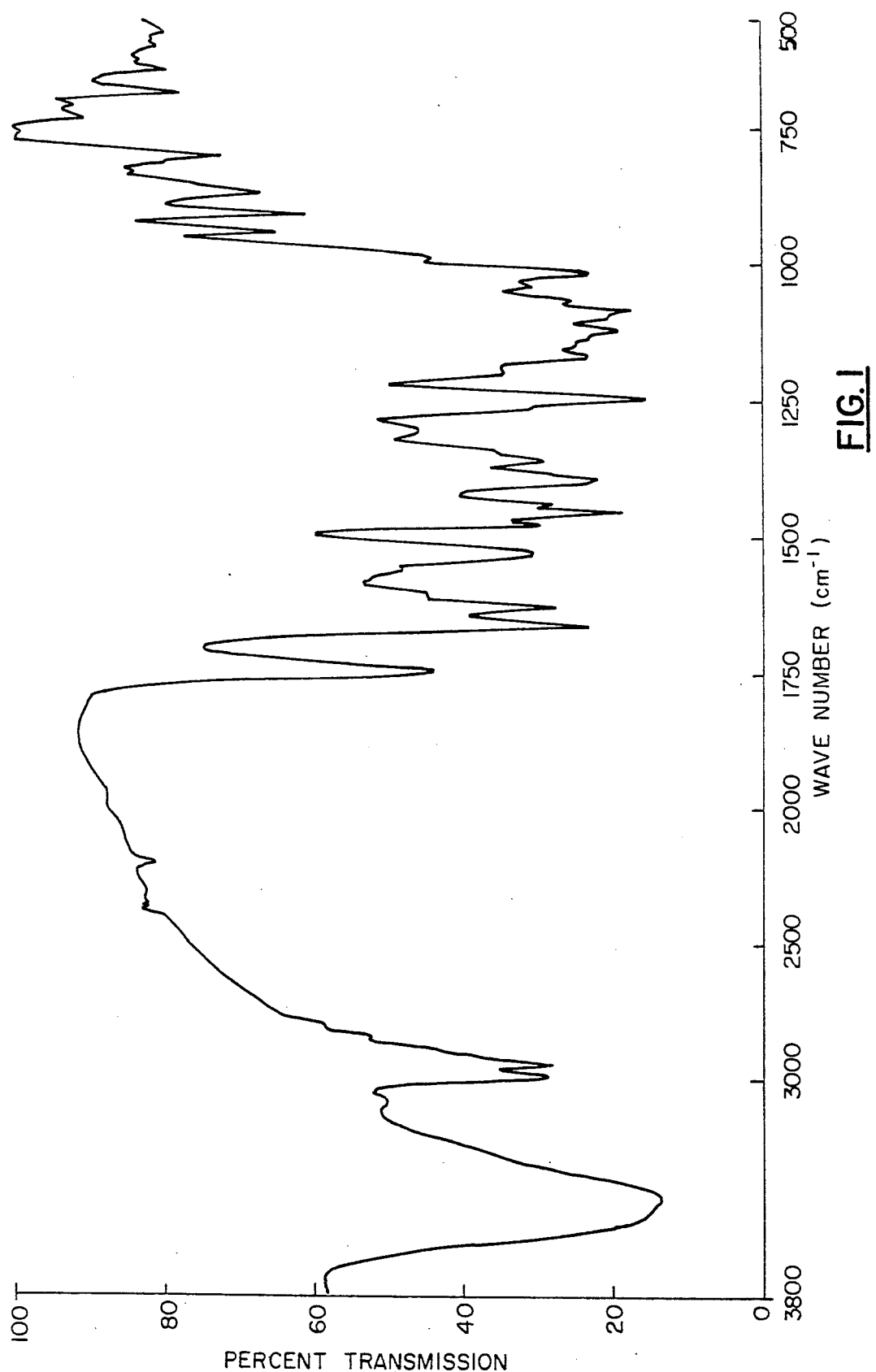
FIG. 1 shows the infrared absorption spectrum of kedarcidin chromophore (KBr pellet).

The kedarcidin chromophore may be obtained from the antitumor antibiotic kedarcidin isolated in U.S. Pat. No. 5,001,112 or from the fermentation broth used to produce kedarcidin. One preferred starting material is purified kedarcidin isolated and purified as described in Example 4 of the above-mentioned U.S. patent. Another preferred starting material is obtained by filtering the fermentation broth cultured with a kedarcidin-producing strain of Streotoalloteichus, subjecting the filtrate to anionic-exchange chromatography using as eluant a cationic buffer in the pH range of 7-8 followed by the same buffer containing sodium chloride, and collecting the fraction eluted with the NaCl buffer. The eluate resulting from this chromatographic procedure has many of the impurities removed and results in higher yields of the desired kedarcidin chromophore. I have found it convenient to lyophilize this eluate for storage prior to the extraction step described below, but the aqueous eluate can be used directly as well. The filtered fermentation broth can also be used in the process of the present invention without the anion exchange purification step, but this requires additional purification steps to obtain the chromophore and is much less efficient than starting with purified kedarcidin or with the partially purified fermentation broth which has been subjected to an anion exchange step.

An aqueous solution of purified or partially purified kedarcidin as described above is then subjected to organic extraction with ethyl acetate. Other organic solvents such as the acidic methanol used to obtain the chromophore of neocarzinostatin, n-butanol, benzene-methanol and chloroform-methanol resulted in decomposition or formation of emulsions. The ethyl acetate extract is then subjected to silica gel liquid chromatography using as the eluant a step gradient of benzene containing increasing concentrations of methanol. The fractions are monitored by thin layer chromatography (TLC) and the desired fraction containing the purified kedarcidin chromophore may then be concentrated in vacuo to obtain the product as a buff-colored amorphous solid.

Physico-chemical Properties of Kedarcidin Chromophore

The kedarcidin chromophore has the following physico-chemical characteristics:

Description: Buff-colored amorphous solid

Stability: Very unstable. Decomposes within hours when in solution with benzene, methanol, chloroform and dimethyl sulfoxide (DMSO).

Molecular Formula: $C_{53}H_{60}N_3O_{16}Cl$
Molecular Weight: 1029.3628
Mass Spectrum: Kratos MS50 Mass Spectrometer $[M+H]^+$ 1030, FAB using m-nitrobenzyl alcohol Infrared Spectrum: Perkin Elmer 1800 Fourier Transform IR Spectrometer; KBr Pellet. Major IR Bands ($cm^{-1}$): 3432, 3076, 2976, 2832, 2188, 1742, 1656, 1622, 1524, 1470, 1450, 1434, 1386, 1354, 1298, 1240, 1192, 1164, 1114, 1080, 1060, 1032, 1010, 980, 936, 902, 862, 824, 798, 680.

Ultraviolet Spectrum: Hewlett Packard 8452A Diode Array Spectrophotometer $\lambda$max (MeOH): 256, 316 nm (log $\epsilon$4.78, 4.16)

Analytical HPLC: Column: Q-BEX C18 (10$\mu$) #10230. Eluant: 4 parts tetrahydrofuran; 6 parts 0.2M ammonium acetate. Flow: 2 ml/min. Detector: 254 nm. Sample concentration: 4 $\mu$g/$\mu$l methanol. Retention time: 12 min.

Elemental analysis: Found: C, 58.78; H, 5.78; N, 3.56. Qualitative test for Cl: positive. Qualitative test for S: negative.

$^1$H-NMR Bruker Model AM-500 Spectrometer. Solvent: DMSO-d6. Observed Chemical Shifts (relative to DMSO signal $\delta$2.531): 1.09 (s, 3H), 1.16 (s br, 6H), 1.34 (s br, 6H), 1.74 (m, 2H), 1.92 (m, 1H), 2.05 (d, 1H, J=14.3), 2.36 (m, 1H), 2.46 (s, 6H), 2.86 (m, 2H), 3.21 (m, 1H), 3.78 (s, 3H), 3.95 (s, 3H), 3.95 (m, 1H), 4.04 (m, 1H), 4.09 (m, 1H), 4.12 (m, 1H), 4.27 (m, 1H), 4.30 (m, 1H), 4.34 (m, 1H), 4.53 (s br, 1H), 4.75 (m, 1H), 4.81 s br, 1H), 5.11 (s br, 1H), 5.44 (s br 1H), 5.56 (m, 1H), 6.19 (s, 1H), 6.62 (s, 1H), 6.97 (s, 1H), 7.11 (s, 1H), 7.22 (d, 1H, J=8.3), 8.06 (d, 1H, J=8.3), 8.48 (s, 1H), 9.56 (d, 1H, J=7.4).

$^{13}$C-NMR: Bruker Model AM-500 Spectrometer. Solvent: DMSO-d6. Observed Chemical Shifts (relative to DMSO signals $\delta$ 39.113, 39.268, 39.447, 39.601, 39.780, 39.935, 40.113):

| Signal | PPM | Multiplicity |
|---|---|---|
| 1 | 17.13 | q |
| 2 | 18.25 | q |
| 3 | 21.86 | q |
| 4 | 27.19 | q |
| 5 | 36.38 | t |
| 6 | 37.62 | t |
| 7 | 41.64 | t |
| 8 | 44.63 | q |
| 9 | 48.31 | d |
| 10 | 49.94 | d |
| 11 | 60.71 | q |
| 12 | 61.62 | q |
| 13 | 64.05 | d |
| 14 | 64.24 | t |
| 15 | 65.57 | d |
| 16 | 65.96 | d |
| 17 | 68.45 | s |
| 18 | 68.93 | d |
| 19 | 70.11 | d |
| 20 | 71.85 | s |
| 21 | 71.91 | d |
| 22 | 76.22 | d |
| 23 | 78.46 | d |
| 24 | 83.14 | d |
| 25 | 88.16 | s |
| 26 | 94.64 | d |
| 27 | 99.81 | d |
| 28 | 99.91 | s |
| 29 | 102.13 | d |
| 30 | 103.96 | s |
| 31 | 109.79 | s |
| 32 | 110.01 | d |
| 33 | 115.86 | s |
| 34 | 117.10 | s |
| 35 | 120.06 | d |
| 36 | 122.80 | d |
| 37 | 123.99 | d |
| 38 | 129.02 | s |
| 39 | 134.33 | s |
| 40 | 136.22 | d |
| 41 | 139.02 | s |
| 42 | 139.10 | d |
| 43 | 141.40 | s |
| 44 | 144.46 | s |
| 45 | 146.28 | s |
| 46 | 148.43 | s |
| 47 | 153.29 | s |
| 48 | 155.17 | s |
| 49 | 155.37 | s |
| 50 | 167.24 | s |
| 51 | 169.06 | s |

Thin Layer Chromatography: $R_f$ 0.29 Benzene-Methanol 9:2
$R_f$ 0.16 Benzene-Methanol 9:1
Plate: Uniplate Silica Gel GHLF, 0.25 mm thickness (Analtech)
Detection: Short wavelength UV light; ceric sulfate spray reagent Based on the above-described physicochemical characteristics, the structure of kedarcidin chromophore is believed to be

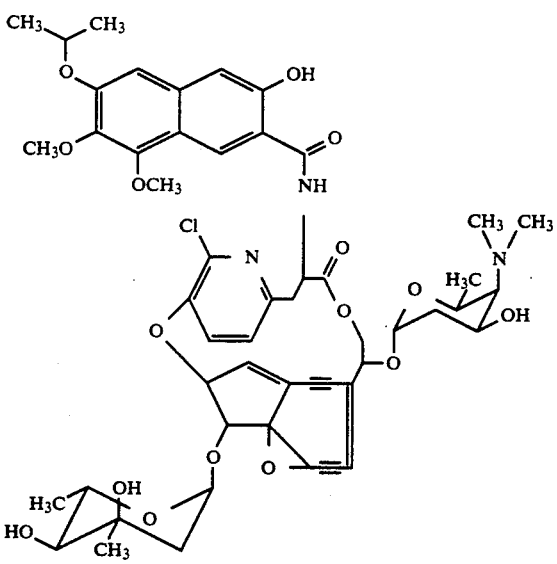

Biological Activity

The antitumor activity of kedarcidin chromophore was evaluated in an in vitro cytotoxicity assay against several human tumor cell lines and in vivo against transplantable murine P388 leukemia and B-16 melanoma. A description of the methods employed and results obtained is provided below.

I. Methods

A. In vitro Cytotoxicity Assay

The cell lines used to evaluate in vitro cytotoxic potency include the human colon adenocarcinoma HCT116 drug sensitive line, HCT 116/VP35 and HCT116/VM46 daughter drug resistant cell lines that have low Topoisomerase II and elevated P-170 glycoprotein levels[1]; respectively, and the human ovarian carcinoma A2780 drug sensitive and the A2780/DDP daughter drug resistant cell line. The A2780/DDP cell line is reported to be resistant through enhanced DNA repair mechanisms and elevated GSH/GST levels. Cells were cultured in McCoy's media and 10% fetal bovine serum. When in log phase growth, $4 \times 10^3$ cells/well were plated into 96 well microtiter plates and incubated at 37° C. in 95% $O_2$/5% $CO_2$ for 24 hours to allow cell attachment. Compounds were added to the top row of wells, serially diluted (4 fold dilutions) and incubated for an additional 72 hours. The number of viable cells in each well was then quantitated as previously described[2] by adding 0.05 mg/ml final concentration tetrazolium stain (XTT) in the presence of 0.005 mM final concentration phenazine methosulfate. After incubation at room temperature for 3 hours to allow color development, optical density values were measured using a Dynatech MR600 plate reader at 450 nM. IC50 values (drug concentration inhibiting cell growth by 50%) were calculated using linear regression analysis of the optical density readings. Triplicate determinations on separate 96 well plates were done for each drug on each cell line tested.

B. Murine In Vivo Models

1. P388 Murine Leukemia Models

The P388 tumor was maintained in ascitic form in DBA/2 mice. Experimental tumor models used CDF[1] mice implanted via the intraperitoneal or intravenous route with $1 \times 10^6$ leukemia cells on day 0 and dosed with drugs according to the indicated route and schedule. Mice were weighed on day 0 and on day 5 or 6. Weight loss of 20% or greater was an indicator of drug toxicity. Each dose group consisted of 6 mice with 10 mice in the untreated control group. The dosing schedule was Q1DX1;1. Death checks were performed daily and the median life span of each group determined. An increase in lifespan of 25% or greater of the drug treated group compared to untreated control mice was the criteria for activity (%T/C>125%). Experiments were terminated on or about day 30.

2. B-16 Murine Solid Tumor Model

The B-16 murine melanoma was maintained as a subcutaneous growing tumor in C57BL/6 mice. Experimental tumor models used BDF[1] mice implanted with a 25 mg tumor fragment implanted subcutaneously via trochar on day 0. Kedarcidin chromophore was administered iv on a Q1DX1;1 schedule. Mice were weighed on day 0 and on day 9.

II. RESULTS

A. In vitro

As shown in the table below, kedarcidin chromophore was extremely potent (compared to VP-16 (etoposide)) in its ability to inhibit cell growth (IC50 values expressed as nanograms of compound/ml, final concentration). Kedarcidin chromophore was 285 and 1725 fold more potent than VP-16 on the two VP-16 sensitive cell lines. In addition, kedarcidin chromophore was not cross-resistant with VP-16 on the HCT116/VP35 or HCT116/VM46 cell lines. When evaluated on the A2780 sensitive and A2780/DDP cell lines, both VP-16 and kedarcidin chromophore were about 6.6 fold less potent on the resistant cell line compared to the sensitive cell line.

In Vitro Cytotoxicity of Kedarcidin Chromophore IC50 (ng/ml)

| Compound | Cell Lines | | | | |
|---|---|---|---|---|---|
| | HCT116 | HCT116/ VP35 | HCT116/ VM46 | A2780 | A2780/ DDP |
| Kedarcidin Chromophore | 0.4 | 0.3 | 0.3 | 0.2 | 1.3 |
| VP-16[a] (etoposide) | 690 | 8758 | 3255 | 57 | 379 |

[a]Vp-16 values are the mean values of triplicate determinations from the last 6 experiments

B. In Vivo

1. P388 Murine Leukemia Model

When evaluated against the ip implanted P388 murine leukemia, kedarcidin chromophore produced a T/C% of 175 at an optimal dose of 1 mg/kg/inj when administered ip one day after tumor implant. In the same experiment, iv implanted P388 tumor cells were also sensitive to the antitumor effects of kedarcidin chromophore. When administered iv one day after tumor implant, kedarcidin chromophore produced a T/C% of 214 at an optimal dose of 0.25 mg/kg/inj. Two different lots of kedarcidin were equally efficacious although somewhat less potent when compared to kedarcidin chromophore in this experiment. The antitumor activity of kedarcidin chromophore against the P388 murine leukemia was confirmed in Experiment 8328. In the ip implanted model, kedarcidin chromophore administered ip, Q1DX1;1 produced a T/C% of 185 at an optimal dose of 0.25 mg/kg/inj. In the iv implanted portion of this experiment, kedarcidin chromophore produced a T/C% of 186 at an optimal dose of 0.125 mg/kg/inj when administered iv on the same schedule. Two different lots of kedarcidin were equally efficacious, if somewhat less potent compared to kedarcidin chromophore in this experiment.

In the P388 murine leukemia models kedarcidin chromophore was both potent and efficacious, regardless of whether the ip, ip model or the iv, iv model was used to evaluate the antitumor activity of this compound. Kedarcidin chromophore was as efficacious as, and slightly more potent than, kedarcidin in the P388 model.

2. B-16 Murine Solid Tumor Model

In Experiment 796, the antitumor activity of kedarcidin chromophore was evaluated using the B-16 murine melanoma model. When the tumor was implanted subcutaneously, kedarcidin chromophore was active by the lifespan criterion with a T/C% of 164 when administered iv one day after tumor implant at an optimum dose of 0.062 mg/kg/inj. In the same experiment kedarcidin produced an identical T/C% at an optimum dose of 0.75 mg/kg/inj using the same route and schedule. Neither kedarcidin chromophore or kedarcidin were active by the tumor growth delay criterion.

III. CONCLUSIONS

Kedarcidin chromophore showed significant antitumor activity in the ip or iv implanted P388 murine leukemia model and in the sc implanted B-16 murine melanoma model by lifespan criterion. It was as active as, and slightly more potent than, kedarcidin when compared directly in these experiments.

IV. REFERENCES

1. Long, B. H., Wang, L., Lorico, A., Wang, R. C. C., Brattain, M. G. and Casazza, A. M. Mechanisms of Resistance to Etoposide and Teniposide in Acquired Resistant Human Colon and Lung Carcinoma Cell Lines. *Cancer Research* 51; In Press (1991).
2. Scudiero, D. A., Shoemaker, R. H., Paull, K. D., Monks, A., Tierney, S., Nofziger, T. H., Currens, M. J., Seniff, D. and Boyd, M. R. Evaluation of a Soluble Tetrazolium/Formazan Assay for Cell Growth and Drug Sensitivity in Culture Using Human and Other Tumor Cell Lines. *Cancer Research* 48: 4827–4833 (1988).

The test results indicate that kedarcidin chromophore displays potent antitumor in vitro activity against several human tumor cell lines and in vivo antitumor activity against murine leukemia P388 and B16 melanoma.

| Antitumor activity against ip implanted P388 leukemia (Exp. 8305) | | | | | |
|---|---|---|---|---|---|
| Lot | mg/kg/ dose or dilution | Med. surv. time | % T/C | Av. wgt. change (g) | No. of mice alive on d 5 |
| Mitomycin C | 4.8 | 23.0 | 230 | −0.7 | 6/6 |
|  | 3.2 | 20.0 | 200 | −0.5 | 6/6 |
| Kedarcidin | 1.6 | 18.5 | 185 | −1.3 | 6/6 |
| 26596-48-1 | 0.8 | 17.0 | 170 | −0.9 | 6/6 |
|  | 0.4 | 16.0 | 160 | −0.8 | 6/6 |
|  | 0.2 | 15.0 | 150 | −0.0 | 6/6 |
|  | 0.1 | 14.0 | 140 | 0.3 | 6/6 |
|  | 0.05 | 13.5 | 135 | 0.8 | 6/6 |
| Kedarcidin | 1.6 | 17.5 | 175 | −0.9 | 6/6 |
| 29190-85-1 | 0.8 | 17.5 | 175 | −0.3 | 6/6 |
|  | 0.4 | 15.0 | 150 | 0.2 | 6/6 |
|  | 0.2 | 14.0 | 140 | 0.3 | 6/6 |
|  | 0.1 | 13.5 | 135 | 0.5 | 6/6 |
|  | 0.05 | 14.0 | 140 | 1.4 | 6/6 |
| Kedarcidin chromophore | 4 | 9.0 | 90 | −3.6 | 6/6 |
|  | 2 | 10.5 | 105 | −2.2 | 6/6 |
|  | 1 | 17.5 | 175 | −0.3 | 6/6 |
|  | 0.5 | 16.5 | 165 | −0.5 | 6/6 |
|  | 0.25 | 15.0 | 150 | −0.4 | 6/6 |
|  | 0.125 | 14.5 | 145 | 0.1 | 6/6 |
| Control |  | 10.0 | 100 | 2.5 | 10/10 |

| Antitumor activity against iv implanted P388 leukemia (Exp. 8305) | | | | | |
|---|---|---|---|---|---|
| Lot | mg/kg/ dose or dilution | Med. surv. time | % T/C | Av. wgt. change (g) | No. of mice alive on d 5 |
| Mitomycin C | 4.8 | 13.5 | 193 | −0.8 | 6/6 |
|  | 3.2 | 11.0 | 157 | 0.5 | 6/6 |
|  | 1.6 | 10.0 | 143 | −0.3 | 6/6 |
|  | 0.8 | 8.0 | 114 | 0.4 | 6/6 |
| Kedarcidin | 1.6 | 6.5 | 93 | −6.0 | 6/6 |
| 26596-48-1 | 0.8 | 12.5 | 179 | −3.0 | 6/6 |
|  | 0.4 | 11.0 | 157 | −0.0 | 6/6 |
|  | 0.2 | 9.0 | 129 | 0.5 | 6/6 |
|  | 0.1 | 8.0 | 114 | −0.3 | 6/6 |
|  | 0.05 | 7.0 | 100 | −0.5 | 6/6 |
| Kedarcidin | 1.6 | 7.0 | 100 | −4.8 | 6/6 |
| 29190-85-1 | 0.8 | 13.0 | 186 | −2.0 | 6/6 |
|  | 0.4 | 11.0 | 157 | −0.3 | 6/6 |
|  | 0.2 | 9.0 | 129 | −0.0 | 6/6 |
|  | 0.1 | 8.5 | 121 | −0.2 | 6/6 |
|  | 0.05 | 7.5 | 107 | −0.0 | 6/6 |
| Kedarcidin chromophore | 4 | TOX | TOX | — | 0/6 |
|  | 2 | TOX | TOX | — | 0/6 |
|  | 1 | TOX | TOX | — | 0/6 |
|  | 0.5 | 7.5 | 107 | −2.9 | 6/6 |
|  | 0.25 | 15.0 | 214 | −0.8 | 6/6 |
|  | 0.125 | 13.0 | 186 | −0.3 | 6/6 |
| Control |  | 7.0 | 100 | −0.1 | 10/10 |

| Antitumor activity against ip implanted P388 leukemia (Exp. 8328) | | | | | |
|---|---|---|---|---|---|
| Lot | mg/kg/ dose or dilution | Med. surv. time | % T/C | Av. wgt. change (g) | No. of mice alive on d 5 |
| Mitomycin C | 4.8 | 20.0 | 200 | −0.5 | 6/6 |
|  | 3.2 | 19.0 | 190 | −0.8 | 6/6 |
| Kedarcidin chromophore | 2.0 | TOX | TOX | −1.9 | 2/6 |
|  | 1.0 | 9.0 | 90 | −2.3 | 6/6 |
|  | 0.5 | 13.0 | 130 | −1.1 | 6/6 |
|  | 0.25 | 18.5 | 185 | −0.4 | 6/6 |
| Kedarcidin Q257 | 2.0 | 22.0 | 220 | −1.1 | 5/6 |
|  | 1.0 | 21.0 | 210 | −0.8 | 6/6 |
|  | 0.5 | 15.5 | 155 | −0.5 | 6/6 |
|  | 0.25 | 17.0 | 170 | −1.0 | 6/6 |
| Kedarcidin W-4 | 8.0 | 18.0 | 180 | −1.4 | 6/6 |
|  | 4.0 | 18.0 | 180 | −1.3 | 6/6 |
|  | 2.0 | 17.5 | 175 | −0.8 | 6/6 |
|  | 1.0 | 16.0 | 160 | −1.0 | 6/6 |
|  | 0.5 | 14.5 | 145 | −0.9 | 6/6 |
|  | 0.25 | 14.5 | 145 | −0.3 | 6/6 |
| Control |  | 10.0 | 100 | 0.8 | 10/10 |

| Antitumor activity against iv implanted P388 leukemia (Exp. 8328) | | | | | |
|---|---|---|---|---|---|
| Lot | mg/kg/ dose or dilution | Med. surv. time | % T/C | Av. wgt. change (g) | No. of mice alive on d 5 |
| Mitomycin C | 3.2 | 10.0 | 143 | −0.7 | 6/6 |
|  | 1.6 | 9.0 | 129 | −0.1 | 6/6 |
| Kedarcidin chromophore | 1.0 | TOX | TOX | — | 0/6 |
|  | 0.5 | TOX | TOX | — | 0/6 |
|  | 0.25 | 7.0 | 100 | −2.4 | 6/6 |
|  | 0.125 | 13.0 | 186 | −2.5 | 6/6 |
| Kedarcidin Q257 | 2.0 | 7.0 | 100 | −5.6 | 6/6 |
|  | 1.0 | 9.5 | 136 | −4.7 | 6/6 |
|  | 0.5 | 13.0 | 186 | −1.7 | 6/6 |
|  | 0.25 | 9.0 | 129 | −0.7 | 6/6 |
| Kedarcidin W-4 | 8.0 | 7.0 | 100 | −5.4 | 6/6 |
|  | 4.0 | 11.5 | 164 | −3.6 | 6/6 |
|  | 2.0 | 11.5 | 164 | −0.9 | 6/6 |
|  | 1.0 | 9.0 | 129 | −0.9 | 6/6 |
|  | 0.5 | 8.0 | 114 | −0.0 | 6/6 |
|  | 0.25 | 7.0 | 100 | −0.1 | 6/6 |
| Control |  | 7.0 | 100 | −0.5 | 10/10 |

| Antitumor activity against sc implanted B16 melanoma (Exp. 796) | | | | | |
|---|---|---|---|---|---|
| Lot | mg/kg/ dose or dilution | Med. surv. time | % T/C | Av. wgt. change (g) | No. of mice alive on d 5 |
| Kedarcidin chromophore | 0.5 | TOX | TOX | — | 0/8 |
|  | 0.25 | TOX | TOX | −1.0 | 2/8 |
|  | 0.125 | 31.5 | 126 | 1.1 | 8/8 |
|  | 0.062 | 41.0 | 164 | 1.1 | 8/8 |
| Kedarcidin Q257 | 1.5 | TOX | TOX | −4.7 | 1/8 |
|  | 0.75 | 41.0 | 164 | 0.7 | 8/8 |
|  | 0.32 | 40.5 | 162 | 0.8 | 8/8 |
|  | 0.16 | 39.0 | 156 | 0.4 | 8/8 |
| Kedarcidin W-4 | 6 | TOX | TOX | −7.7 | 2/8 |
|  | 3 | 47.5 | 190 | −0.7 | 8/8 |
|  | 1.5 | 36.5 | 146 | 0.0 | 8/8 |
|  | 0.75 | 31.0 | 124 | 0.0 | 8/8 |
| Control |  | 25.0 | 100 | −0.2 | 10/10 |

The invention includes within its scope pharmaceutical compositions containing an effective tumor-inhibiting amount of kedarcidin chromophore in combination with a pharmaceutically acceptable carrier of diluent. Such compositions may also contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antitumor agent, optimal dosages and regimens for a given mammalian host can be readily ascertained by those skilled in the art. It will, of course, be appreciated that the actual dose used will vary according to the particular composition formulated, the route of administration and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The present invention is illustrated by the following example which is not intended to be construed as limiting the scope of the invention. Unless otherwise indicated, all solvent ratios are vol/vol.

EXAMPLE 1

General Methods

Materials

Chloroform, benzene, ethyl acetate, and methanol were anhydrous ACS grade solvents. Tetrahydrofuran was preservative-free HPLC grade solvent. These solvents were not repurified or redistilled. Water used in solvent partition experiments refers to in-house deionized water. Water used in chromatography experiments refers to inhouse deionized water passed through a Millipore 4 cartridge reagent grade water system (10 mega ohm MilliQ water). Ammonium acetate was HPLC grade reagent. Silica gel for vacuum liquid chromatography was Merck LiChroprep Si 60, particle size 25-40 μm. Cerium sulfate hydrate and ammonium molybdate (VI) tetrahydrate are ACS grade reagents.

Analytical Thin Layer Chromatography (TLC)

Uniplate Silica Gel GHLF precoated thin layer chromatography plates (scored 10×20 cm, 250 microns) were used. Fractions were spotted using size 2 microliter Microcaps (disposable pipets) and the plates were developed in a tank equilibrated with benzene-methanol (9:2 v/v). The components of the resulting chromatogram were visualized by short wavelength UV light and/or ceric sulfate spray reagent.

Ceric Sulfate Spray Reagent

Ceric sulfate spray reagent for thin layer chromatography was prepared by dissolving 6 g of cerium sulfate hydrate and 28 g of ammonium molybdate (VI) tetrahydrate in 20% aqueous sulfuric acid (500 ml). The sprayed TLC plate was developed by heating at approximately 150° C. for 5-10 minutes.

Analytical HPLC

The following components were used to construct an analytical HPLC system: Waters Associates, Model M-45 solvent delivery system; Waters Associates, Model U6K injector; Waters Associates, Guard-Pak Precolumn Module with C18 cartridge; Q-BEX Scientific Inc. C18 (10 micron) column (3.9 mm i.d.×30 cm, QBX-10230). The components were connected with 316 stainless steel tubing (1.6 mm o.d.–0.23 mm i.d.). The specified eluant was pumped at a flowrate of 2.0 ml/min. Detection was with a Hewlett Packard HP-1040A Detector System. This system consisted of a Hewlett Packard HP-1040A Diode Array Detector, HP-85B Computer, HP-9121 Disc Drive and a HP-7470 plotter.

Purification of Kedarcid Chromophore

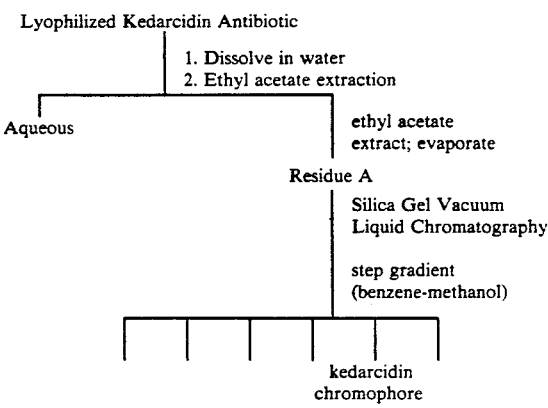

Preparation of Extract A

Kedarcidin fermentation broth is obtained following the general procedures of Examples 1-3 U.S. Pat. No. 5,001,112. The raw fermentation broth is subjected to filtration and anion exchange chromatography to obtain the eluate described at column 13, line 34 of U.S. Pat. No. 5,001,112. This eluate containing partially purified kedarcidin antibiotic is employed, after lyophilization, as the starting material in the following extraction step.

Partially purified lyophilized kedarcidin (76 g) prepared by lyophilization of the eluate described above was dissolved in 1100 ml water. The aqueous solution was extracted four times with an equal volume of ethyl acetate using a 6L separatory funnel. The ethyl acetate extracts were pooled and evaporated in vacuo to dryness in a rotary evaporator to yield 0.34 g of residue A.

Vacuum Liquid Chromatography of Residue A

A small Kontes fritted filter funnel (2.5 cm i.d. ×11 cm) was packed three-quarters full with dry silica gel (Merck LiChroprep 25-40 μm), 12 g. The column was equilibrated with 100 ml benzene using inhouse vacuum to elute the solvent. Residue A was dissolved in ethyl acetate-methanol 3:1 (5 ml) and preadsorbed onto 3 g silica gel. The sample was slurried in benzene, transferred to the column and the vacuum applied. Using a step gradient, elution was begun (100 ml each) with benzene, 1% methanol in benzene, 2%, 5%, and 7.5% methanol in benzene (3 times). The chromatogram was monitored with TLC using short wavelength UV light and ceric sulfate spray reagent for visualization. The desired substance eluted with the first 100 ml of 7.5% methanol in benzene. This fraction was evaporated to dryness in vacuo (25° C.) in a rotary evaporator to yield 0.2 g kedarcidin chromophore.

Figure 2:
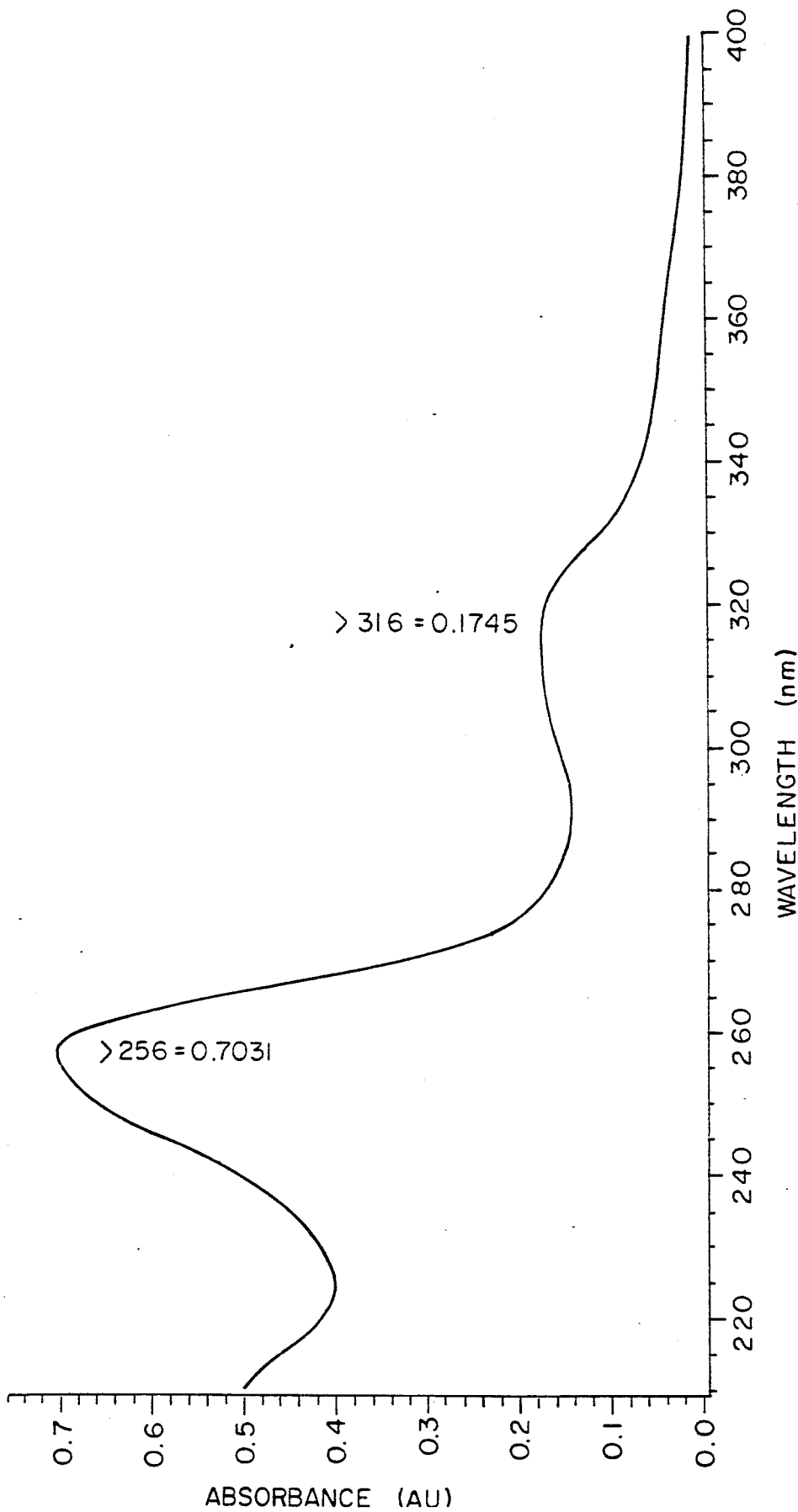
FIG. 2 shows the ultraviolet absorption spectrum of kedarcidin chromophore when dissolved in methanol.
Figure 3:
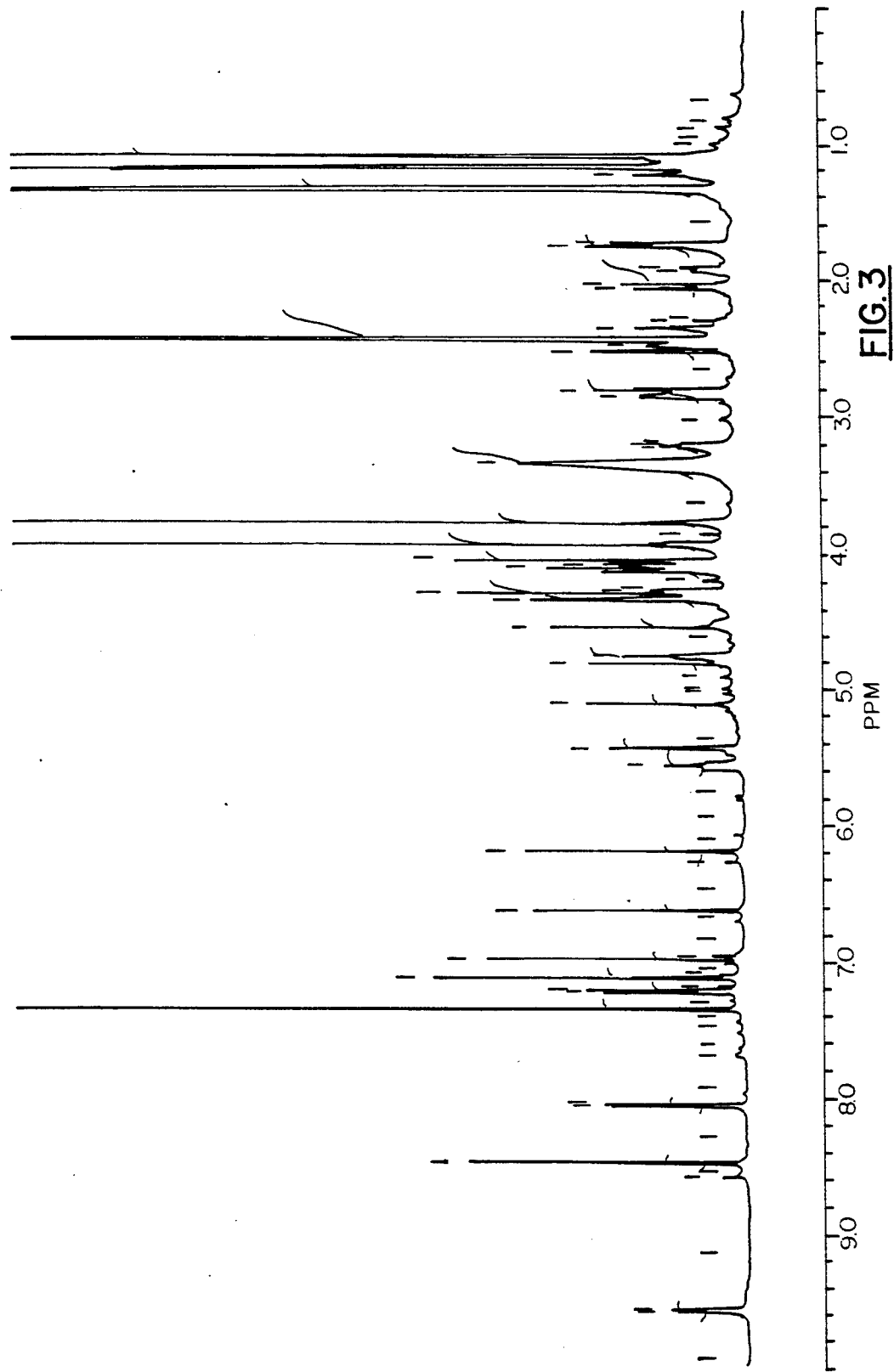
FIG. 3 shows the proton magnetic resonance spectrum of kedarcidin chromophore in DMSO-d6 (500.13 MHz).
Figure 4:
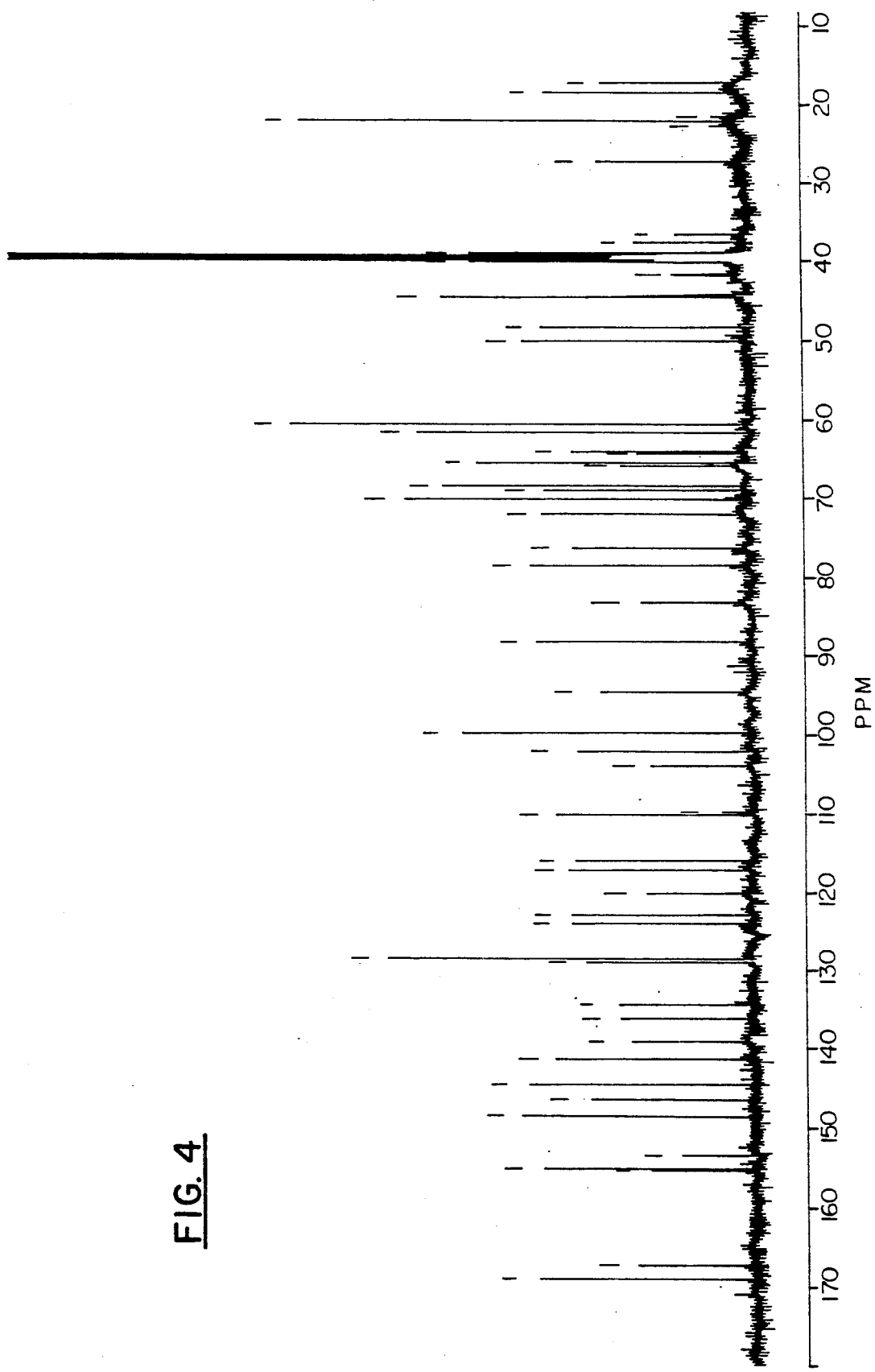
FIG. 4 shows the $^{13}C$ magnetic resonance spectrum of kedarcidin chromophore in DMSO-d6 (125.76 MHz).

What is claimed is:

1. The antibiotic designated kedarcidin chromophore characterized as follows:

(a) appears as a buff-colored amorphous solid;

(b) has a molecular weight of 1029 as determined by mass spectroscopy;

(c) has the molecular formula $C_{53}H_{60}N_3O_{16}Cl$;

(d) exhibits an infrared absorption spectrum (KBr) substantially as shown in FIG. 1;

(e) exhibits an ultraviolet absorption spectrum when dissolved in methanol substantially as shown in FIG. 2;

(f) when dissolved in DMSO-d6 exhibits a proton magnetic resonance spectrum substantially as shown in FIG. 3;

(g) when dissolved in DMSO-d6 exhibits a $^{13}C$ magnetic resonance spectrum substantially as shown in FIG. 4;

(h) exhibits in silica gel thin layer chromatography an Rf value of 0.29 with the solvent system benzene-methanol (9:2 v/v) and an Rf value of 0.16 with the solvent system benzene-methanol (9:1 v/v);

(i) exhibits a high performance liquid chromatography retention time of 12 minutes with a $C_{18}$ reversed phase silica gel column and the solvent system tetrahydrofuran - 0.2M ammonium acetate (2:3 v/v); and has the formula

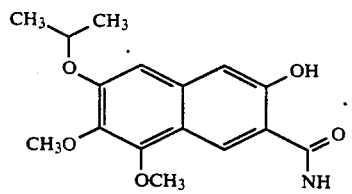

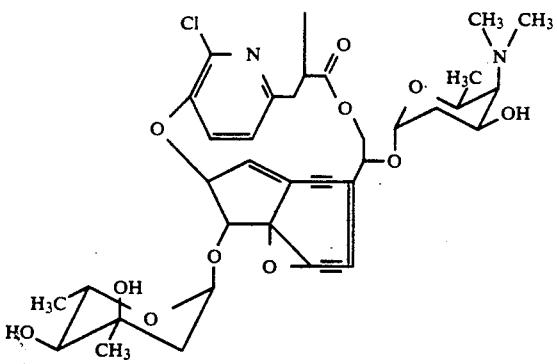

2. A pharmaceutical composition which comprises a tumor-inhibiting amount of kedarcidin chromophore having the formula

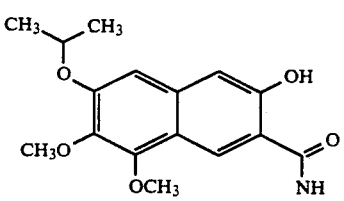

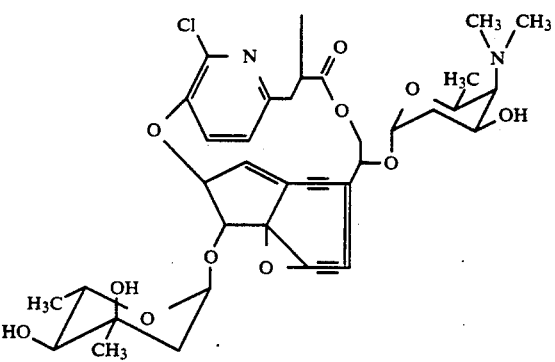

and a pharmaceutically acceptable carrier or diluent.

* * * * *